United States Patent [19]

Kent et al.

[11] 4,135,818

[45] * Jan. 23, 1979

[54] PLATELET AGGREGATION MONITORING DEVICE

[75] Inventors: Frederick M. Kent, Warrington; Michael Sokol, Abington, both of Pa.

[73] Assignee: Bio/Data Corporation, Willow Grove, Pa.

[*] Notice: The portion of the term of this patent subsequent to Nov. 2, 1993, has been disclaimed.

[21] Appl. No.: 703,993

[22] Filed: Jul. 9, 1976

Related U.S. Application Data

[63] Continuation-in-part of Ser. No. 542,997, Jan. 22, 1975, Pat. No. 3,989,382.

[51] Int. Cl.² .................... G01N 33/16; G01N 21/24; G01D 9/08
[52] U.S. Cl. ........................................ 356/39; 346/62; 356/427
[58] Field of Search ............ 356/39, 197, 208; 73/64.1; 324/71 CP; 23/230 B; 346/62; 307/360

[56] References Cited

U.S. PATENT DOCUMENTS

| | | | |
|---|---|---|---|
| 3,548,206 | 12/1970 | Ogle et al. | 324/71 CP |
| 3,836,333 | 9/1974 | Mintz | 23/230 B |
| 3,861,877 | 1/1975 | Matharani et al. | 356/39 |
| 3,905,769 | 9/1975 | Carroll et al. | 23/230 B |
| 3,965,477 | 6/1976 | Hambleton et al. | 346/62 |
| 3,989,382 | 11/1976 | Kent et al. | 356/39 |

FOREIGN PATENT DOCUMENTS 830766  3/1960  United Kingdom ............... 307/360

Primary Examiner—John K. Corbin
Assistant Examiner—Wm. H. Punter
Attorney, Agent, or Firm—Seidel, Gonda & Goldhammer

[57] ABSTRACT

A difference amplifier continuously generates a signal representing the difference between the optical densities of a platelet rich and a platelet poor sample of blood plasma. If this signal lies within a predetermined range, a variable gain amplifier multiplies the difference signal by a factor which is proportional to the initial difference signal. Electronic circuitry automatically determines the multiplying factor by comparing the initial difference signal to a predetermined magnitude. The multiplied difference signal is continuously recorded on a chart recorder and is displayed as a percentage of aggregation on a digital display. An optional filter circuit is provided for selectively filtering the difference signal.

4 Claims, 3 Drawing Figures

PLATELET AGGREGATION MONITORING DEVICE

CROSS-REFERENCE TO RELATED APPLICATION

This application is a continuation-in-part of our co-pending prior application Ser. No. 542,997 filed Jan. 22, 1975 now U.S. Pat. No. 3,989,382.

The present invention relates to a platelet aggregation monitoring device and more particularly to a device which monitors, records and displays platelet aggregation by measuring the optical densities of a platelet rich and a platelet poor sample of blood plasma and continuously generating a signal representing the difference between the two measured optical densities.

The blood platelet plays a unique roll in the maintenance of normal hemostasis and in the initiation of clot formation. Briefly, following injury to a blood vessel wall, the damaged vessel has exposed connective tissue to which platelets, which are cells found in the blood, adhere. This activity is known as platelet adhesion.

Once the platelets stick to exposed tissue, they then adhere to each other. The adhesion of platelets to each other, as distinct from their adhesion to foreign surfaces, is known as platelet aggregation. The initiation of platelet aggregation occurs as a result of the exposed collagen in the endothelium of the blood vessel. As the platelets aggregate, they release endogeneous ADP (adenosine diphosphate). The released endogeneous ADP further causes the platelets to aggregate.

Methods of studying platelet aggregation in vitro have been known for some time. In the most frequently used method, platelet aggregation is recorded as the increase in light transmission which occurs when platelet aggregates form in a stirred platelet rich plasma. Platelet rich plasma (PRP) is turbid due to the presence of platelets in suspension. When the platelets aggregate, the turbidity decreases. A light beam is directed through the PRP and the percent transmission or optical density is recorded on a reader such as a chart recorder. Platelet aggregation is initiated by the addition of various reagents such as ADP and collagen. With normal platelets, two waves of aggregation may be obtained. This will depend on the type and concentration of the reagent used. The first wave is due to the direct affect of the reagent and the second wave is the result of the ADP released from the platelets.

Platelet aggregation monitoring devices which carry out the above-described method are also known in the art. However, these prior art devices all suffer from the same basic limitations. Their sensitivity is either fixed or manually adjustable and they, therefore, cannot automatically compensate for the differences in optical densities between plasma samples from different patients. Additionally, these devices use platelet poor plasma only as an initial reference and do not continuously monitor the difference between platelet rich and platelet poor specimens. This may decrease the accuracy of the device and increases the time required for instrument set-up and standardization.

When making platelet aggregation measurements, one is not primarily concerned with the number of platelets in the sample but rather the concern is with the manner in which the platelets aggregate. The number of platelets, however, affects the optical density of the sample. Furthermore, the optical density in a plasma sample from one patient may be substantially different from a similar sample taken from a second patient even though the number of platelets may be the same. This is caused by a plurality of factors including bilirubin and lipemia in the plasma and set-up or adjustment error on the part of the operator.

Thus, prior art devices having a manually adjusted sensitivity may be capable of monitoring platelet aggregation activity in some samples but incapable of accurately monitoring platelet aggregation activity in other samples without manual readjustment. In addition, they require a substantial amount of set-up time since the 0% and 100% baselines must be adjusted prior to each test if full scale deflection is desired. Thus, it is the primary purpose of the present invention to provide a platelet aggregation monitoring device which automatically adjusts its sensitivity for full scale deflection for each sample being measured and which eliminates operator errors and errors which may be caused by other substances in the samples. The invention also provides several safeguard features which prevent a test from being run unless certain predetermined conditions are met.

The invention accomplishes the above by providing a difference amplifier which continuously generates a signal representing the difference between the optical densities of a platelet rich and a platelet poor sample of blood plasma. If this signal lies within a predetermined range, a variable gain amplifier multiples the difference signal by a factor which is proportional to the initial difference signal. Electronic circuitry automatically determines the multiplying factor by comparing the initial difference signal to a predetermined magnitude. A chart recorder continuously records the multiplied difference signal and the signal is also displayed as a percentage of aggregation on a digital display.

For the purpose of illustrating the invention, there is shown in the drawings a form which is presently preferred; it being understood, however, that this invention is not limited to the precise arrangements and instrumentalities shown.

Figure 1:
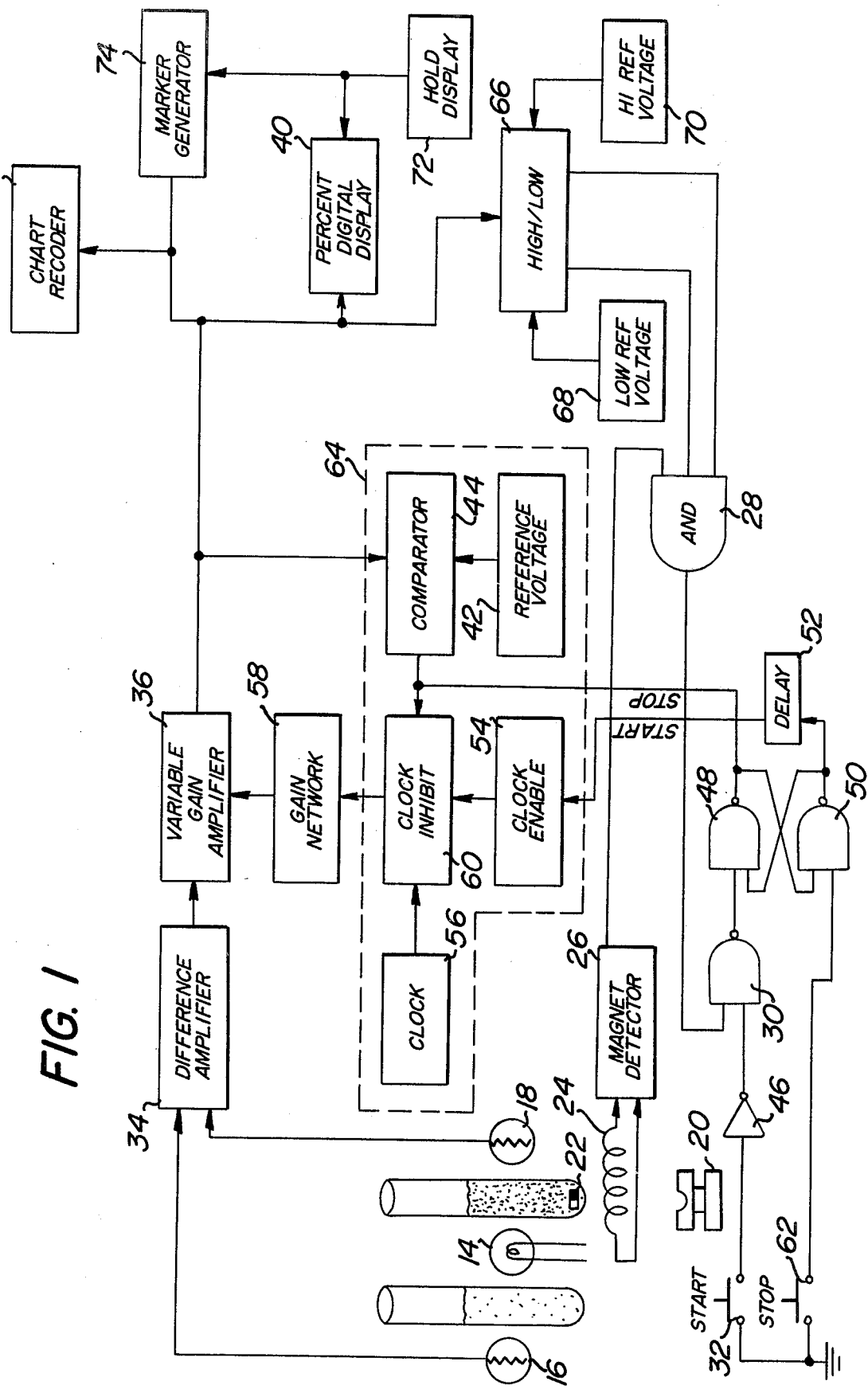
FIG. 1 is a block diagram of a preferred means for carrying out the present invention.

Referring now to the drawings in detail, there is shown in FIG. 1 a block diagram of a circuit for carrying out the present invention. As shown, test tubes 10 and 12 are positioned between a common light source 14 and photosensitive means such as photo-resistors 16 and 18, respectively. Test tube 10 contains a platelet poor plasma (PPP) sample and test tube 12 contains a platelet rich plasma (PRP) sample to which an aggregating agent such as ADP is to be added. These samples are prepared in a manner well known in the art.

The contents of test tube 12 are continuously mixed by magnetic stirrer 20. Mixing is effected in a known manner by magnetic stirrer 20 acting on a small magnet 22 which is placed in the bottom of test tube 12 containing the PRP sample. Since the aggregation test will not be accurate unless the PRP sample is properly stirred, a means is provided for ensuring that the operator of the device has not forgotten to place the magnet 22 in the test tube 12. This circuit is comprised of an induction coil 24 located adjacent to the bottom of test tube 12 and in the magnetic field of magnetic stirrer 20 and magnet 22. The sinusoidal signal across coil 24 produced by the rotating magnetic field is rectified and compared to a predetermined threshold value in magnet detector circuit 26. In the absence of magnet 22, the voltage across coil 24 would be above the threshold voltage and the output of magnet detector circuit 26 will be low. Accordingly, the output of AND gate 28 will also be low. Since the output of AND gate 28 is connected to one input of NAND gate gate 30, this will inhibit any start signal from start switch 32 from starting the test. With magnet 22 properly in position, the voltage across coil 24 is reduced below the threshold voltage and the output of magnet detector circuit 26 will be high allowing the instrument to start if other initial conditions described above are met.

The output signals from photo-resistors 16 and 18, which signals represent the optical densitities of the PPP and PRP samples, respectively, are fed to the inputs of difference amplifier 34. The output of difference amplifier 34, therefore, represents the difference in the optical densities of the PPP and PRP samples. Since only the difference in the optical densities of the PPP and PRP samples is utilized, the effect of factors such as bilirubin and lipemia or the like in the samples which may effect the optical density are eliminated. This difference signal is then amplified by variable gain amplifier 36 and is thereafter recorded on chart recorder 38 and additionally is displayed as a percentage of aggregation on display 40.

Figure 2:
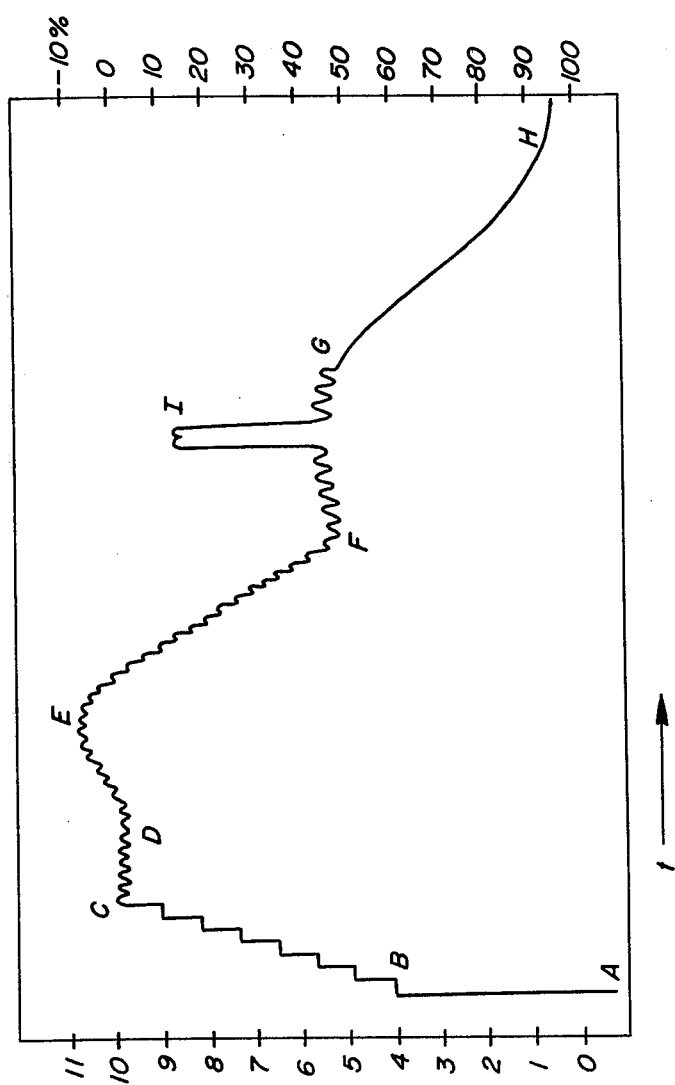
FIG. 2 is a graph illustrating a typical electrical output signal generated by the circuit shown in FIG. 1.

According to the principles of the present invention, the PPP sample is considered to be the zero reference and a standard difference is established on the chart recorder 38 between PPP and PRP. This standard desired difference is preferably at a point near full scale on the chart recorder 38. For example, as shown in FIG. 2, the standard difference represents ten major divisions on the chart. This corresponds to a voltage at the output of amplifier 36 of 10 volts. The eleventh major division on the chart recorder 38 is not utilized as the starting point since as a result of platelet swelling and oscillations caused by the agitation of the PRP sample, the optical density of the PRP sample may increase slightly before it begins to decrease. This increase is shown in FIG. 2 at point E. Thus, if the eleventh major division on the chart were chosen to represent the desired constant difference then the optical density shown at point E would not appear.

Referring again to FIG. 1, the initial standard difference is established by comparing the output of variable gain amplifier 36 to a fixed reference voltage 42 by comparator circuit 44. The platelet aggregation monitoring device is initially started by depressing start switch 32 which through inverter 46 and NAND gate 30 causes the flip-flop comprised of NAND gates 48 and 50 to generate a pulse at the output of gate 50. After a three to five second delay to allow the photo-resistors to stabilize, which delay is caused by delay circuit 52, clock enable circuit 54 is activated and the gain of the variable gain amplifier 36 begins to increase stepwise. Each step increase is caused by a pulse from clock 56 entering gain network circuit 58. Eventually, the gain of variable gain amplifier 36 increases sufficiently so that its output is equal to the reference voltage 42 which as stated above is approximately 10 volts corresponding to ten major divisions on the chart of chart recorder 38. When this favorable comparison is sensed by comparator circuit 44, clock inhibitor circuit 60 prevents further clock pulses from clock 56 from passing to the gain network circuit 58. Thereafter, for the remainder of the test, the gain of variable gain amplifier remains constant. The test will stop after a preselected time interval or may be stopped by depressing stop button 62 which, through flip-flop 48, 50, activates clock inhibit circuit 60. The foregoing circuits and their operation are described more fully in applicants' co-pending application Ser. No. 542,997 now U.S. Pat. No. 3,989,382. In particular, all of the circuits within the broken line box 64 are shown in detail in FIG. 5 of said application.

To ensure that the initial platelet concentration of the PRP sample is within the operating range of the instrument, the circuit also includes a high/low comparator 66. High/low comparator circuit 66 includes a pair of threshold detectors and is connected through appropriate gating means to the output of variable gain amplifier 36. Comparator 66 is also connected to a low reference voltage source 68 and a high reference voltage source 70. It has been found that best results are obtained if the initial platelet concentration is neither too high nor too low. Optimally, the initial platelet concentration of the PRP sample should be such that the initial output of the variable gain amplifier 36 (before the automatic gain circuit takes over) should be between approximately 1 and 9 volts. Accordingly, high/low comparator circuit 66 includes a first threshold detector having a threshold of 1 volt and a second threshold detector having a threshold of 9 volts. Since the outputs of comparator 66 are connected to AND gate 28, if the initial output of variable gain amplifier 36 is below 1 volt or above 9 volts, the output of gate 28 will go low causing gate 30 to inhibit the start of the test. If, however, the initial output signal of variable gain amplifier 36 is between 1 and 9 volts, then the test will proceed as described above.

Thus, it can be seen that the above-described circuit automatically provides a continuous differential comparison of the optical densities of the PRP and PPP samples thereby reducing the time required for instrument set-up and standardization. In addition, the circuit automatically standardizes the chart recorder for full scale deflection thereby eliminating the need for manual adjustment and readjustment of the chart recorder baseline. Even further, as described in detail below, the percent digital display circuit 40 automatically and continuously displays the percentage of platelet aggregation so that both the aggregation curve and the percentage of aggregation can be observed while the test is being run.

FIG. 2 represents the output of variable gain amplifier 36 as recorded on chart recorder 38. The vertical axis on the left represents the voltage and the major divisions on the chart paper. The vertical axis to the right represents the percentage of aggregation as displayed by circuit 38. Point A on the curve represents zero optical difference which means that the difference in the optical density between the PPP sample and the PRP sample is zero. Before any tests are run in the device, the light system and difference amplifier circuit 34 can be calibrated by replacing test tubes 10 and 12 with test tubes containing water or any other substance so that the tubes have equal density and adjusting the several components until the output of variable gain amplifier 36 is zero. Point B on the graph represents the initial difference in the optical densities between the PPP and PRP samples. Since the difference in the optical densities is within the proper operating range of the instrument, i.e., between one and nine divisions on the chart, the gain of the variable gain amplifier 36 is automatically increased in a stepwise progression as described above until the gain of the amplifier 36 is such that the needle of the chart recorder 38 is at the tenth division on the graph. This is equal to 10 volts or 0% of aggregation and is represented by letter C in FIG. 2. At point D on the graph, the ADP or other aggregating agent is added to the PRP sample and the remaining parts of the graph represent the difference in the optical densities between the PPP and PRP samples as the platelets aggregate in the PRP sample.

As described above, after the addition of the aggregating reagent at point D, the platelets may swell causing an increase in density as shown at point E. The output of amplifier 36 thus rises to 11 volts which is represented at the right as minus 10% aggregation. It can also be seen that there are two waves of aggregation. The first is between points E and F and is caused by the aggregating reagent. The second wave can be seen between points G and H and is caused by intrinsic ADP released by the platelets themselves as they aggregate. The graph between points F and G represents a cessation of aggregation and in some instances may show disaggregation prior to intrinsic ADP release if it occurs.

As stated above, the percentage of platelet aggregation is continuously displayed by display 40. However, it may, at times, be desirable to know precisely the percentage of aggregation when a certain event occurs as observed on the graph of chart recorder 38. This is accomplished by depressing a hold display switch 72 which temporarily holds the digital display then present at display circuit 40. The test and the chart recorder 38, however, continue to run uninterrupted. At the same time that the hold display button 72 is depressed, a marker generator 74 generates a pulse which causes the pen of chart recorder 38 to jump momentarily at the appropriate place to aid in interpretation. This is shown at point I on the graph in FIG. 2. After the graph has been marked and the percentage displayed by display 40 is noted, the hold display button 72 is released. Percentage digital display circuit 40 automatically catches up to the present value indicated at the output of variable gain amplifier 36 and continues to display the percentage of platelet aggregation.

Figure 3:
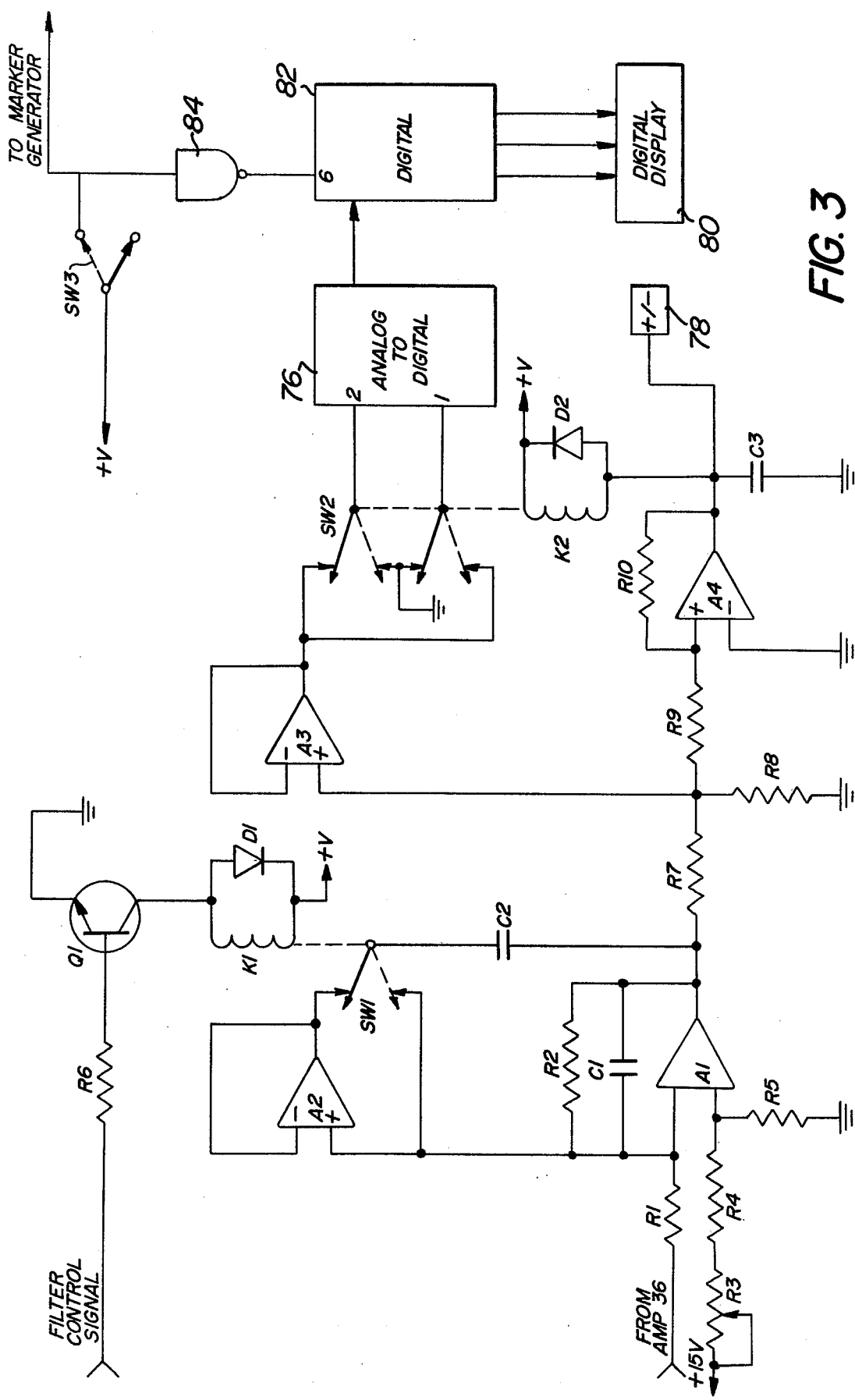
FIG. 3 is a schematic diagram of a preferred form of the percent digital display circuit shown in FIG. 1.

FIG. 3 is a schematic diagram showing a preferred form of the percent digital display circuit shown in FIG. 1. As seen in FIG. 3, the output of variable gain amplifier 36 is fed to the inverting input of operational amplifier A1 through resistor R1. Amplifier A1 functions as a unity gain inverter and scaler. Accordingly, feedback resistor R2, connected between the output of amplifier A1 and the inverting input has the same value as input resistor R1. Also connected between the output of amplifier A1 and the inverting input is a capacitor C1 which is used to limit the high frequency response. A voltage divider network comprised of variable resistor R3 and fixed resistors R4 and R5 is connected at the junction of resistors R4 and R5 to the non-inverting input of amplifier A1. The remote end of variable resistor R3 is connected to a positive 15 volt source and the values of resistors R3, R4 and R5 are selected such that a positive voltage of 5 volts is maintained at the non-inverting input to amplifier A1. As a result of the above-described configuration, as the input voltage to resistor R1 (i.e., the output of variable gain amplifier 36) decreases from 10 volts to 0 volts, the output of amplifier A1 increases from 0 volts to 10 volts. Furthermore, it can be seen that if the input voltage to resistor R1 increases above 10 volts, the output of amplifier A1 will go negative. For example, an output voltage of 11 volts from variable gain amplifier 36 will result in an output voltage of amplifier A1 of −1 volt.

As stated above, the input to amplifier A1 represents the difference in the optical densities between the PRP and PPP samples and includes oscillations which are caused by the fact that the PRP sample is constantly being stirred. These oscillations will cause the digital display of the percentage of aggregation to become erratic and difficult to observe. Accordingly, the unity gain inverting and scaling amplifier circuit described above is provided with a filter in the feedback leg of the amplifier.

The filter is comprised essentially of a large capacitor C2 which may, when desired, be switched out of the feedback leg of amplifier A1. Since it is desired to prevent the filter capacitor C2 from causing any significant shifting in the output signal of amplifier A1 when the filter is switched into the circuit, a buffer amplifier A2 is used to maintain the capacitor charge voltage at the proper level. Buffer amplifier A2 is connected as a non-inverting, unity gain amplifier, which has a very high input impedance. When switch SW1 is in the position shown by the solid line in FIG. 3, capacitor C2 is effectively not in the feedback circuit since it has approximately 10 meg ohms in series with it. However, buffer amplifier A2 functions as a very low impedance voltage source and charges capacitor C2 so that when capacitor C2 is switched into the feedback path of amplifier A1, there is little or no effect on the average D.C. output of amplifier A1.

Filter capacitor C2 is switched into the feedback path of amplifier A1 when switch SW1 is in the position shown by the broken lines in FIG. 3. Switch SW1 is part of relay K1. One side of the coil of relay K1 is connected to a positive voltage source and the other side of the coil is connected to the collector of transistor Q1. A diode D1 is also connected across the coil of relay K1. The emitter of transistor Q1 is connected to circuit ground. One side of resistor R6 is connected to the base of transistor Q1 and the other side is connected to the clock inhibit and clock enable circuits 60 and 54. In the preferred embodiment, the connection is made to the output of NAND gate 50 shown in FIG. 5 of applicants' co-pending application Ser. No. 542,997 now U.S. Pat. No. 3,989,382. Thus, it can be seen that the filter capacitor C2 is switched into the feedback loop of amplifier A1 only after the gain of variable gain amplifier 36 has been automatically set and is out of the feedback loop during the 3 to 5 second delay and during the time that the automatic gain network is being adjusted.

Referring again to amplifier A1, it will be recalled that the output thereof goes from 0 to 10 volts. However, the analog to digital converter circuit utilized with the present invention and described more fully below, requires an input of 0 to +1 volt. Accordingly, a voltage divider circuit comprised of resistors R7 and R8 provides the necessary division so that the voltage at the junction of resistors R7 and R8 represents the output of amplifier A1 divided by 10. This signal is also fed to the non-inverting input of buffer amplifier A3. The output of amplifier A3 is fed through an automatic polarity switching circuit to the input of analog to digital subsystem circuit 76. Circuit 76 may be, for example, a Motorola MC1405L or similar circuit.

The automatic polarity switching circuit is necessary since the input to analog to digital circuit 76 can accept only positive analog signals at pin 2 with respect to pin 1 and it will be recalled that the output of amplifier A1 and therefore the output of amplifier A3 will go negative if the input to amplifier A1 increases above 10 volts. The automatic polarity switching circuit is comprised essentially of a DPDT switch SW2 which forms part of relay K2. FIG. 3 shows switch SW2 in its normal position when relay K2 is not energized which is the proper polarity position for feeding positive analog signals from the output of amplifier A3 to the input of analog to digital subsystem circuit 76. The dotted lines shown in FIG. 3 show the switch SW2 in its reverse polarity position when relay K2 is energized. In this position, negative analog signals from the output of amplifier A3 can be fed to the input of circuit 76.

Relay K2 and thus switch SW2 is controlled by an automatic polarity sensing circuit comprised essentially of comparator amplifier A4. Input resistor R9 is connected between the junction of resistors R7 and R8 to the non-inverting input of amplifier A4. Feedback resistor R10 is connected to the output of amplifier A4 and the non-inverting input thereof. Capacitor C3 is connected between the output of amplifier A4 and ground and the inverting input to amplifier A4 is grounded. The output of amplifier A4 is connected to one side of the coil of relay K2. The other side of the coil of relay K2 is connected to a positive voltage source. A diode D2 is also connected across the coil of relay K2. Thus, when the voltage at the junction of resistors R7, R8 and R9 goes negative, the output of comparator amplifier A4 goes low causing relay K2 to conduct thereby closing switch SW2. The output of amplifier A4 is also connected to a sign indicator display 78. Indicator display 78 normally displays either a plus sign or no sign at all and displays a minus sign whenever the output of amplifier A4 goes low. The display 78 is positioned adjacent (or may be incorporated in) digital display 80 and indicates whether the numerals displayed thereon represent positive or negative percentages.

The output of analog to digital subsystem circuit 76 is connected to a digital subsystem circuit 82. Circuit 82 may be, for example, a Motorola MC14435VP or similar circuit. The output of digital subsystem circuit 82 is a multiplexed signal which is fed to the digital display 80. Circuits 76, 82 and the digital display 80 and their interconnections are conventional and accordingly will not be described in detail. A typical arrangement is shown, for example, in FIG. 5 of Motorola advance information specification ADI-303.

As described above, a hold display switch is provided for temporarily holding the digital display at any desired point and for simultaneously marking the chart recorder 36. This hold display switch is comprised of a switch SW3 shown in the upper righthand corner of FIG. 3. Switch SW3 is movable between the positions shown in the solid and dotted lines in FIG. 3. When the switch is in a position shown in solid lines, a positive voltage is applied to the display update input 6 of circuit 82 through gate 84. In this position, circuit 82 functions normally to process the signals at the input thereof. When switch SW3 is thrown to the position shown in dotted lines in FIG. 3, however, the output of gate 84 goes low. As a result, circuit 82 ceases to process the incoming signals and the digital display at display 80 is held at its present value. Simultaneously, a positive voltage is sent through switch SW3 to the marker generator where a mark is made on the graph of the chart recorder at the appropriate place to aid in interpretation thereof. Thereafter, switch SW3 is returned to its original position shown in solid lines in FIG. 3 and circuit 82 automatically updates the digital display at display 80.

The values of the various components used in the circuit of FIG. 3 are shown in the table below. It should be noted, however, that these values merely represent the preferred embodiment of the invention and that various other components and circuit arrangements could obviously be substituted without departing from the spirit and scope of the present invention.

Table

| | | | |
|---|---|---|---|
| R1 = 100K | C1 = .001µfd | D1 = 1N4454 | Q1 = 2N3646 |
| R2 = 100K | C2 = 11µfd | D2 = 1N4454 | |
| R3 = 2K | C3 = .47µfd | | |
| R4 = 9.1K | | | |
| R5 = 5.1K | | | |
| R6 = 2.2K | | | |
| R7 = 9.1K | | | |
| R8 = 1K | | | |
| R9 = 2.2K | | | |
| R10 = 910K | | | |

The present invention may be embodied in other specific forms without departing from the spirit or essential attributes thereof and, accordingly, reference should be made to the appended claims, rather than to the foregoing specification as indicating the scope of the invention.

We claim:

1. In a platelet aggregation monitoring device comprising:
    electro-optical means for continuously generating a signal representing the difference in the optical densities of a platelet rich plasma sample and a platelet poor plasma sample;
    electronic means for multiplying said signal by a variable factor;
    electronic means for automatically adjusting said factor such that said multiplied signal is equal to a pre-selected standard value, whereby the sensitivity of the device is automatically adjusted;
    electronic means for maintaining said factor constant once it has been adjusted to the point that said multiplied signal is equal to said preselected standard value;
    the improvement comprising electronic means for determining whether or not said signal, representing the difference between the optical density of a platelet rich plasma and a platelet poor plasma, lies within a preselected range prior to its being multiplied by said variable factor and inhibiting the operation of said platelet aggregration monitoring device if said signal does not lie within the preselected range.

2. In a platelet aggregation monitoring device in accordance with claim 1:
    magnetic means for stirring said platelet rich plasma sample including a magnet adapted to be positioned within said platelet rich sample and means for generating a rotating magnetic field for rotating said magnet within said platelet rich sample;
    the improvement further comprising means for sensing the presence or absence of said magnet and inhibiting the operation of said platelet aggregation monitoring device if said magnet is absent, said inhibiting means including means for inhibiting the operation of said platelet aggregation monitoring device unless said signal is within a preselected range and said magnet is present.

3. In a platelet monitoring device in accordance with claim 1, the improvement further comprising;

electronic means for processing and continuously digitally displaying said multiplied signal as a percentage of platelet aggregation;

said processing means including means for filtering out oscillations in said signal caused by the stirring of the platelet rich sample; and switching means for activating said filter means only after said factor has been set at the constant value.

4. In a platelet aggregation monitoring device as claimed in claim 3, the improvement further comprising means for temporarily holding the digital display at a particular percentage value and for simultaneously marking the record produced by a recording means with a mark indicative of said value.

* * * * *